(12) United States Patent
Pelczar et al.

(10) Patent No.: US 8,633,348 B2
(45) Date of Patent: Jan. 21, 2014

(54) GENETIC VASECTOMY BY OVEREXPRESSION OF PRML-EGFP FUSION PROTEIN IN SPERMATIDS

(75) Inventors: Pawel Pelczar, Egg (CH); Thorsten Buch, München (DE); Antoine Peters, Basel (CH)

(73) Assignees: Novartis Forschungsstiftung, Zweigniederlassung, Friedrich Miescher Institute for Biomedical Research, Basel (CH); Universität Zürich, Zürich (CH)

( * ) Notice: Subject to any disclaimer, the term of this patent is extended or adjusted under 35 U.S.C. 154(b) by 11 days.

(21) Appl. No.: 13/392,145

(22) PCT Filed: Aug. 26, 2010

(86) PCT No.: PCT/EP2010/062437
§ 371 (c)(1),
(2), (4) Date: Mar. 28, 2012

(87) PCT Pub. No.: WO2011/023740
PCT Pub. Date: Mar. 3, 2011

(65) Prior Publication Data
US 2012/0180151 A1    Jul. 12, 2012

(30) Foreign Application Priority Data
Aug. 28, 2009  (EP) .................................. 09168969

(51) Int. Cl.
*A01K 67/027* (2006.01)
*C12N 15/00* (2006.01)

(52) U.S. Cl.
USPC ...................... 800/18; 800/1; 800/14; 800/21

(58) Field of Classification Search
None
See application file for complete search history.

(56) References Cited

U.S. PATENT DOCUMENTS 5,223,610 A    6/1993  Burton

FOREIGN PATENT DOCUMENTS

WO    WO 99/10488 A1    3/1999
WO    WO 01/62076 A1    8/2001

OTHER PUBLICATIONS

Peschonn JJ et al, "Expression of mouse protamine 1 genes in transgenic mice", Annals of NY Academy Sciences, vol. 664, pp. 188-197 (1989).
Peschon JJ et al, "Spermatid-specific expression of protamine 1 in transgenic mice", Procedures of the National Academy of Sciences USA, vol. 84, No. 15, pp. 5316-5319 (1987).
Braun RE et al, "Protamine 3'-untranslated sequences regulate temporal translational control and subcellular localization of growth hormone in spermatids of transgenic mice", Genes and Development, vol. 3, No. 6, pp. 793-802 (1989).
Brain RE et al, "Genetically haploid spermatids are phenotypically diploid", Nature, vol. 337, pp. 373-376 (1989).
Zhong et al, "A highly conserved sequenced essential for translational repression of the protamine 1 messenger RNA in murine spermatids", Biology of Reproduction, vol. 64, No. 6, pp. 1784-1789 (2001).
Fajardo MA et al, "Germ Cell-Specific Proteins Interact with the 3' Untranslated Regions of Prm-1 and Prm-2 mRNA", Developmental Biology, vol. 166, No. 2, pp. 643-653 (1994).
Stewart TA et al, "Haploid-specific transcription of protamine.nyc and protamine-T-antigen fusion genes in transgenic mice", Molecular and Cellular biology, vol. 8, No. 4, pp. 1748-1755 (1988).
Rhim JA et al, "Expression of an avian protamine in transgenic mice disrupts chromatin structure in spermatozoa", Biology of Reproduction, vol. 52, No. 1, pp. 20-32 (1995).
Lee K et al, "Premature translation of protamine 1 mRNA causes precocious nuclear condensation and arrests spermatid differentiation in mice", Proceedings of the National Academy of Science USA, vol. 92, pp. 12451-12455 (1995).
Oliva, R, "Protamines an dmale infertility", Human Reproduction Update, vol. 12, No. 4, pp. 417-435 (2006).
Behringer RR et al, "Heart and bone tumors in transgenic mice", Proceedings of the National Academy of Science USA, vol. 85, No. 8, pp. 2648-2652 (1988).
Aivatiadou E et al, "Impaired fertility and spermiogentic disorders with loss of cell adhesion in male mice expressing an interfering Rap1 mutant", Mollecular Biology of the Cell, vol. 18, No. 4, pp. 1530-1542 (2007).
Haueter S et al, "Genetic vasectomy-Overexpression Prm1-EGFP fusion protein in elongating spermatids causes dominant male sterility in mice", Genesis, vol. 48, No. 3, pp. 151-160 (2010).
Magram J et al, "Dominant male sterility in mice caused by insertion of a transgene", Proceedings of the National Academy of Science USA, vol. 88, No. 22, pp. 10327-10331 (1991).
Meng X et al, "Transgene insertion induced dominant male sterility and rescue of male fertility using round spermatid injection", Biology of Reproduction, vol. 66, No. 3, pp. 726-734 (2002).

*Primary Examiner* — Doug Schultz
(74) *Attorney, Agent, or Firm* — Hoxie & Associates LLC (57) ABSTRACT

The present invention provides a genetically-modified non-human animal whose somatic and germ cells contain an exogenous gene encoding a recombinant fusion protein, wherein the presence, and expression, of said recombinant fusion protein renders said genetically-modified non-human animal sterile. Tools for generating such sterile genetically-modified non-human animal as well as methods of use thereof are also provided.

13 Claims, 2 Drawing Sheets

GENETIC VASECTOMY BY OVEREXPRESSION OF PRML-EGFP FUSION PROTEIN IN SPERMATIDS

This application is a National Phase Application of PCT/EP2010/062437, filed on Aug. 26, 2010, which claims benefit of Application No EP09/168,969.5, filed Aug. 28, 2009, which in their entirety are herein incorporated by reference.

FIELD OF THE INVENTION

The present invention relates to genetically-modified non-human animals carrying a fusion protein which renders the homozygous males sterile.

BACKGROUND OF THE INVENTION

Transgenic mice are vital tools in both basic and applied research. Virtually all techniques used to generate transgenic and knock-out mice relay on Embryo Transfer (ET) as a means of producing animals from embryos manipulated in vitro. Strain rederivation by ET is also the most frequent method of eliminating disease pathogens and parasites from laboratory strains of mice. Presently, the ET procedure requires the preparation of pseudopregnant females by mating them with vasectomised males. Only pseudopregnant foster mothers can subsequently implant graft embryos and until now, mating of females with vasectomised males is the only reliable way of inducing pseudopregnancy in mice. The vasectomy procedure is associated with moderate to high pain and must be carried out by trained personnel with the animal receiving full anaesthesia followed by a recovery period and analgesic regime. Eliminating of the need for vasectomy would not only simplify the ET process but is also highly desirable from the animal welfare point of view. One possible strategy would be to use male mice that are capable of copulation but are unable to produce offspring due to a genetic defect in sperm maturation.

To date, a number of genes have been identified which when mutated cause male sterility. Most of these genes are involved in control of DNA recombination, DNA repair or differentiation of the male reproductive tract or the male germline (Bellve A R. *The Molecular Biology of Mammalian Spermatogenesis*, ed. Finn C A., Oxford Univ. Press, London, Vol. 1, pp. 159-261; Brugmans L et al., Mutat. Res., 2007, 614(1-2):95-108; Jaroudi S & SenGupta S., Mutat Res., 2007, 635(1):53-77). Unfortunately, most of these strains are also associated with decreased viability, susceptibility to cancer or other diseases. In addition, strains harbouring such mutations are not good candidates for vasectomy replacement since these recessive traits require breeding and reliable genotyping of heterozygous (fertile) versus homozygous (sterile) male mutant mice. Classical dominant mutations causing male sterility have been described but also none of them appear to be ideally suited for the purpose of replacing surgically vasectomised males in a laboratory environment. These mutants include the Dominant spermiogenesis defect (Dspd) which results from a reciprocal translocation between chromosomes 14 and 7 (Kai M. et al., Biol Reprod., 2004, 70(4): 1213-21) as well as two randomly generated insertional mutations named Lacking vigorous sperm (Lvs) (Magram J. & Bishop J M., Proc Natl Acad Sci USA., 1991, 88(22): 10327-31) and Dominant male sterility (Dms) (Meng X, et al., Biol Reprod., 2002, 66(3):726-34), respectively. Since the genes causing the sterility have not been identified, it is impossible to reproduce the phenotype in other strains. Furthermore, the lack of a phenotypic marker associated with the sterility trait adds the burden of identification of transgenic offspring by genotyping methods.

Dominant male-sterility has also been described in mice overexpressing transgenes. For example, ubiquitous overexpression of the Retinoic acid receptor alpha (Rarα) causes dominant male-sterility due to severe malformation of the epithelium of the reproductive tract (Costa S L, et al., Biol Reprod., 1997, 56(4):985-90). Unfortunately, the perturbation of the epithelium also prevents the formation of the ejaculate. Hence, sterile males fail to produce a copulatory plug, also known as mating plug, copulation plug, vaginal plug, or sphragis, upon mating making the identification of pseudopregnant females virtually impossible.

Overexpression of the Retinits pigmentosa GTPase regulator (Rpgr) protein also leads to male infertility in mice due to defects in flagellar assembly (Brunner S., et al., Biol. Reprod., 2008, 79(4):608-17). Finally, it was shown that premature overexpression of mouse Protamine-1 (Prm1) can cause dominant male sterility. The nuclear protein Prm1, together with its homolog Prm2, play crucial roles in the nuclear reorganization of elongating spermatids during the final stages of sperm development. Protamine proteins ultimately replace the bulk of histones from the genomic DNA and mediate extreme condensation of the sperm genome (Peschon J J. et al., Proc Natl Acad Sci USA., 1987, 84(15):5316-9). The Prm1 gene is transcribed in round spermatocytes, while the resulting mRNA is translated about 4 days later in late elongating spermatids. This translational delay is brought about by regulatory elements residing in the 3'UTR of the Prm1 mRNA (Zhong J., et al., Biol. Reprod., 2001, 64(6): 1784-9). Previous studies have shown that premature translation of Prm1 in round spermatids, brought about by replacement of the Prm1 3'UTR with a heterologous 3'UTR, leads to defects in spermatid maturation and results in the absence of sperm and subsequent male sterility (Lee K. et al., Proc. Natl. Acad. Sci. USA., 1995, 92(26):12451-5).

At the time of the invention, there was a need in the art for genetic alternatives for e.g. surgical vasectomy. Some solutions had been proposed. However, some problems still remained. First of all, the sterility phenotype was not fully penetrant in all lines tested, and second, the absence of a visible marker made the identification of mice carrying the transgene difficult.

The present inventors developed a mouse strain that accommodates all these requirements. Transgenic expression of a fusion protein induces dominant sterility with full penetrance. Moreover, the fact that one of the partners of the fusion protein can be a label greatly facilitates the identification of the mice carrying the fusion protein. Alternatively, genetically linking the expression of the fusion protein to ubiquitous label expression in the soma, also provides a reliable and cost-effective procedure, outperforming e.g. the classical surgical vasectomy methodology.

SUMMARY OF THE INVENTION

The present inventors have now surprisingly found that the expression of a fusion protein can induce sterility.

The present invention hence provides a genetically-modified non-human animal whose somatic and germ cells contain an exogenous gene encoding a recombinant fusion protein, wherein the presence, and expression, of said recombinant fusion protein renders said genetically-modified non-human animal sterile. In some cases, the gene encoding a recombinant fusion protein is dominant. Therefore, the presence, and expression, of only one allele said recombinant fusion protein renders said genetically-modified non-human animal sterile.

In some embodiments, the animal is a rodent, for instance a mouse or a rat.

In some embodiments of the invention, the expression product of the gene encoding a recombinant fusion protein hinders spermatogenesis and/or modifies spermatozoa in such a way that they do not support embryonic development after fertilization.

In some embodiments of the invention, the gene encoding for a recombinant fusion protein encodes for a Prm1 gene product, or a Rpgr gene product, operably linked to a fusion partner in said genetically-modified non-human animal. In some embodiments, the genetically-modified non-human animal of the invention is a sterile male and can be used to induce pseudopregnancy in surrogate mothers.

In some embodiments of the invention, the recombinant fusion protein is only expressed upon addition, and/or expression, of a further component. Instances of such a further component are doxycycline and CRE recombinase.

In some embodiments of the invention, the recombinant fusion protein consists of a wild type gene operably-linked to a label so that the structure and/or function of said wild type gene is disrupted by the attachment of said label. In some cases, this label can be a fluorescent label, for instance EGFP. In some embodiments, at least some of the somatic cells of said genetically-modified non-human animal express a label if the gene coding for the recombinant fusion protein is present. In such embodiments, the presence of the label allows for a rapid selection of the genetically-modified non-human animal carrying the gene encoding for the recombinant fusion protein. The label can be a particular phenotype and/or a fluorescent label, for instance EGFP.

The present invention also encompasses an isolated nucleic acid comprising a nucleotide sequence encoding for a Prm1 gene product, or for the gene product of an orthologue or homologue of Prm1, or a Rpgr gene product, or for the gene product of an orthologue or homologue of Rpgr, operably linked to a fusion partner and wherein the expression of said nucleotide sequence hinders spermatogenesis, or the nucleotide sequence complementary to these nucleotide sequences. In said isolated nucleic acid the fusion partner can be a detectable label, for instance a fluorescent protein such as EGFP. Moreover, the isolated nucleic acid of the invention can further comprise a second detectable label, independent from the recombinant fusion protein and operably placed under the control of a promoter which will induce the expression of said second detectable label in at least some of somatic cells.

BRIEF DESCRIPTION OF THE DRAWINGS

FIG. 2: Reproductive performance of transgenic lines. A) Daily plugging frequencies of transgenic and control males as assessed over a period of 30 days (average and standard deviation; n=3 per genotype). Control values were obtained from normal and vasectomised wild-type littermates. B) Daily conception frequencies of transgenic and control males as assessed over a period of 30 days (average and standard deviation; n=3 per genotype).

DETAILED DESCRIPTION OF THE INVENTION

The present inventors have now surprisingly found that the expression of a fusion protein can induce sterility.

The present invention hence provides a genetically-modified non-human animal whose somatic and germ cells contain an exogenous gene encoding a recombinant fusion protein, wherein the presence, and expression, of said recombinant fusion protein renders said genetically-modified non-human animal sterile. In some cases, the gene encoding a recombinant fusion protein of the invention is dominant. Therefore, the presence, and expression, of only one allele said recombinant fusion protein renders said genetically-modified non-human animal sterile. In such cases, it can be of advantage, for instance in order to simplify the generation of the genetically-modified non-human animal of the invention in such a way that that they can be simply bred, if the expression of the dominant gene encoding a recombinant fusion protein only leads to sterility in one gender. For instance, in some embodiments only males expressing the recombinant fusion protein of the invention are sterile, whereas females expressing said recombinant fusion protein remain fertile, or vice versa. Another solution to obtain this effect is the use of a conditionally-expressed recombinant fusion protein, as described below. In this case, the recombinant fusion protein is only expressed upon addition, and/or expression, of a further component, for instance doxycycline or CRE recombinase. There are numerous well-known ways of achieving such conditional mutants, of which the skilled person will choose the one most adapted to his case, without the exercise of any inventive activity. In the case of a not-dominant, i.e. recessive, gene encoding a recombinant fusion protein of the invention, the heterozygous animals will be used for breeding, whereas the homozygous ones will be sterile.

In some embodiments, the animal is a rodent, for instance a mouse or a rat. It is however to be understood that the present invention applies for all animals, except humans.

In some embodiments of the invention, the expression product of the gene encoding a recombinant fusion protein hinders spermatogenesis and/or modifies spermatozoa in such a way that they do not support embryonic development after fertilization. For instance, the gene encoding for a recombinant fusion protein can encode for a Prm1 gene product, or a Rpgr gene product, operably linked to a fusion partner in said genetically-modified non-human animal. Other suitable genes are any protamine. Moreover, the present invention also encompasses fusion products of other gene products implicated in nuclear condensation during spermatogenesis or spermiogenesis, for instance transition proteins, and/or important for the proper development and functioning of spermatozoids.

In some embodiments, the genetically-modified non-human animal of the invention is a sterile male and can be used to induce pseudopregnancy in surrogate mothers. Other uses of the genetically-modified non-human animal of the invention are mentioned herein-below.

In some embodiments of the invention, the recombinant fusion protein is only expressed upon addition, and/or expression, of a further component. Instances of such a further component are doxycycline and CRE recombinase.

In some embodiments of the invention, the recombinant fusion protein consists of a wild type gene operably-linked to a label so that the structure and/or function of said wild type gene is disrupted by the attachment of said label. In some cases, this label can be a fluorescent label, for instance EGFP. In some embodiments, at least some of the somatic cells of said genetically-modified non-human animal express a label if the gene coding for the recombinant fusion protein is present. In such embodiments, the presence of the label allows for a rapid selection of the genetically-modified non-human animal carrying the gene encoding for the recombinant fusion protein. The label can be a particular phenotype, e.g. curly hairs or fur of a particular color, and/or a fluorescent label, for instance EGFP.

The present invention also encompasses an isolated nucleic acid comprising a nucleotide sequence encoding for a Prm1 gene product, or for the gene product of an orthologue or homologue of Prm1, or a Rpgr gene product, or for the gene product of an orthologue or homologue of Rpgr, operably linked to a fusion partner and wherein the expression of said nucleotide sequence hinders spermatogenesis, or the nucleotide sequence complementary to these nucleotide sequences. In said isolated nucleic acid the fusion partner can be a detectable label, for instance a fluorescent protein such as EGFP. Moreover, the isolated nucleic acid of the invention can further comprise a second detectable label, independent from the recombinant fusion protein and operably placed under the control of a promoter which will induce the expression of said second detectable label in at least some of somatic cells. Moreover, the present invention also encompasses (expression) vectors comprising isolated nucleic acid molecules of the invention, as well as cells and viruses comprising such vectors.

The non-human animals of the invention are of outmost utility for inducing pseudo-pregnancy in the process of breeding genetically-modified animals. However, the present invention is not limited to this particular embodiment. Other utilities of the present invention are for instance the generation of sterile pets, or of any animal which for safety or social reasons should not be able to reproduce. In addition, such animals are also useful for the control of wild-type populations. For instance, the release of sterile males can cause the normal breeding of a given population to collapse, at least as long as the sterile males are living. This is especially true when the sterile males have a competitive advantage over the wild-type fertile ones. Moreover, the cells of the non-human animals of the invention can also be used to generate recipient embryos useful for the generation of chimaeric animals. Such a method would promote germline transmission of the donor genetic information. For example, in animals that are chimearic for germ cells expressing and not expressing Prm1-EGFP, the Prm1-EGFP-mediated dominant male sterility is expected to promote transmission of the non-expressing spermatozoa. This strategy could be applied in regular transgenesis by using EGFP-positive pre-implantation embryos, generated by double transgenic Prm1-EGFP; CAG-EGFP females and wild-type males, as recipients for genetically modified embryonic stem cells (ESCs). Full-body CAG-EGFP-based expression of EGFP in the recipient cells can be used to assess the level of chimerism between EGFP-negative ESCs and EGFP-positive recipient cells while Prm1-EGFP-mediated sterility will enable efficient transmission of genetically modified alleles. The versatility in applications of the double transgenic Prm1-EGFP; CAG-EGFP mice will thus guarantee its efficient usage in common transgenesis practise.

Yet another use of the non-human animals of the invention is their use as a recipient for modified spermatogonial stem cells (or germline stem cells), as described for instance in Kanatsu-Shinohara, M., Ogonuki, N., Inoue, K., Miki, H., Ogura, A., Toyokuni, S. and Shinohara, T. (2003). Long-term proliferation in culture and germline transmission of mouse male germline stem cells. Biol. Reprod. 69, 612-616. In this embodiment, spermatogonial stem cells are genetically modified in vitro and then transplanted into the testis of a recipient animal. When the recipient is a non-human animals of the invention, the only viable and fertile sperms produced by the transplanted testis will be the ones originating from said transformed spermatogonial stem cells, thus ensuring that any offspring of the transplanted animal carries the genetic information which was in the transplanted genetically-modified spermatogonial stem cells.

The term "non-human animal" is used herein to include all animals, except humans. In some embodiments of the invention, the non-human animal is a vertebrate. Examples of non-human animals are mice, rats, cows, pigs, horses, chickens, ducks, geese, cats, dogs, etc. The term "non-human animal" also includes an individual animal in all stages of development, including embryonic and fetal stages. A "genetically-modified animal" is any animal containing one or more cells bearing genetic information altered or received, directly or indirectly, by deliberate genetic manipulation at a sub-cellular level, such as by targeted recombination, micro-injection or infection with recombinant virus. The term "genetically-modified animal" is not intended to encompass classical crossbreeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA. The term "germ-line genetically-modified animal" refers to a genetically-modified animal in which the genetic alteration or genetic information was introduced into germ-line cells, thereby conferring the ability to transfer the genetic information to its offspring. If such offspring in fact possess some or all of that alteration or genetic information, they are genetically-modified animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The genes used for altering a target gene may be obtained by a wide variety of techniques that include, but are not limited to, isolation from genomic sources, preparation of cDNAs from isolated mRNA templates, direct synthesis, or a combination thereof.

A type of target cells for transgene introduction is the ES cells. ES cells may be obtained from pre-implantation embryos cultured in vitro and fused with embryos (Evans et al. (1981), Nature 292:154-156; Bradley et al. (1984), Nature 309:255-258; Gossler et al. (1986), Proc. Natl. Acad. Sci. USA 83:9065-9069; Robertson et al. (1986), Nature 322:445-448; Wood et al. (1993), Proc. Natl. Acad. Sci. USA 90:4582-4584). Transgenes can be efficiently introduced into the ES cells by standard techniques such as DNA transfection using electroporation or by retrovirus-mediated transduction. The resultant transformed ES cells can thereafter be combined with morulas by aggregation or injected into blastocysts from a non-human animal. The introduced ES cells thereafter colonize the embryo and contribute to the germline of the resulting chimeric animal (Jaenisch (1988), Science 240:1468-1474). The use of gene-targeted ES cells in the generation of gene-targeted genetically-modified mice was described 1987 (Thomas et al. (1987), Cell 51:503-512) and is reviewed elsewhere (Frohman et al. (1989), Cell 56:145-147; Capecchi (1989), Trends in Genet. 5:70-76; Baribault et al. (1989), Mol. Biol. Med. 6:481-492; Wagner (1990), EMBO J. 9:3025-3032; Bradley et al. (1992), Bio/Technology 10:534-539).

Techniques are available to inactivate or alter any genetic region to any mutation desired by using targeted homologous recombination to insert specific changes into chromosomal alleles.

As used herein, a "targeted gene" is a DNA sequence introduced into the germline of a non-human animal by way of human intervention, including but not limited to, the methods described herein. The targeted genes of the invention include DNA sequences which are designed to specifically alter cognate endogenous alleles.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. However, a nucleic acid contained in a clone that is a member of a library (e.g., a genomic or cDNA library) that has not been isolated from other members of the library (e.g., in the form of a homogeneous solution containing the clone and other members of the library) or a chromosome removed from a cell or a cell lysate (e.g., a "chromosome spread", as in a karyotype), or a preparation of randomly sheared genomic DNA or a preparation of genomic DNA cut with one or more restriction enzymes is not "isolated" for the purposes of this invention. As discussed further herein, isolated nucleic acid molecules according to the present invention may be produced naturally, recombinantly, or synthetically.

"Polynucleotides" can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotides can be composed of triple-stranded regions comprising RNA or DNA or both RNA and DNA. Polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The expression "polynucleotide encoding a polypeptide" encompasses a polynucleotide which includes only coding sequence for the polypeptide as well as a polynucleotide which includes additional coding and/or non-coding sequence.

"Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1× SSC at about 50 degree C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37 degree C. in a solution comprising 6×SSPE (20×SSPE=3M NaCl; 0.2M NaH2PO4; 0.02M EDTA, pH 7.4), 0.5% SDS, 30% formamide, 100 µg/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The terms "fragment," "derivative" and "analog" when referring to polypeptides means polypeptides which either retain substantially the same biological function or activity as such polypeptides. An analog includes a proprotein which can be activated by cleavage of the proprotein portion to produce an active mature polypeptide.

The term "gene" means the segment of DNA involved in producing a polypeptide chain; it includes regions preceding and following the coding region "leader and trailer" as well as intervening sequences (introns) between individual coding segments (exons).

Polypeptides can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include, but are not limited to, acetylation, acylation, biotinylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, denivatization by known protecting/blocking groups, disulfide bond formation, demethylation, formation of covalent cross-links, formation of cysteine, formation of pyroglutamate, formylation, gamma-carboxylation, glycosylation, GPI anchor formation, hydroxylation, iodination, linkage to an antibody molecule or other cellular ligand, methylation, myristoylation, oxidation, pegylation, proteolytic processing (e.g., cleavage), phosphorylation, prenylation, racemization, selenoylation, sulfation, transfer-RNA mediated addition of amino acids to proteins such as arginylation, and ubiquitination. (See, for instance, PROTEINS-STRUCTURE AND MOLECULAR PROPERTIES, 2nd Ed., T. E. Creighton, W.H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182: 626-646 (1990); Rattan et al., Ann NY Acad Sci 663:48-62 (1992).)

A polypeptide fragment "having biological activity" refers to polypeptides exhibiting activity similar, but not necessarily identical to, an activity of the original polypeptide, including mature forms, as measured in a particular biological assay, with or without dose dependency. In the case where dose dependency does exist, it need not be identical to that of the polypeptide, but rather substantially similar to the dose-dependence in a given activity as compared to the original polypeptide (i.e., the candidate polypeptide will exhibit greater activity or not more than about 25-fold less and, in some embodiments, not more than about tenfold less activity, or not more than about three-fold less activity relative to the original polypeptide.)

Species homologs may be isolated and identified by making suitable probes or primers from the sequences provided herein and screening a suitable nucleic acid source for the desired homologue.

"Variant" refers to a polynucleotide or polypeptide differing from the original polynucleotide or polypeptide, but retaining essential properties thereof. Generally, variants are overall closely similar, and, in many regions, identical to the original polynucleotide or polypeptide.

As a practical matter, whether any particular nucleic acid molecule or polypeptide is at least 80%, 85%, 90%, 92%, 95%, 96%, 97%, 98%, 99%, or 100% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Blosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty—1, Joining Penalty—30, Randomization Group Length=0, Cutoff Score=I, Gap Penalty—5, Gap Size Penalty 0.05, Window Size=500 or the length of the subject nucleotide sequence, whichever is shorter. If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 impaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98%, 99%, or 100% identical to, for instance, the amino acid sequences shown in a sequence or to the amino acid sequence encoded by deposited DNA clone can be determined conventionally using known computer programs. A preferred method for determining, the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty—I, Joining Penalty=20, Randomization Group Length=0, Cutoff Score=I, Window Size=sequence length, Gap Penalty—5, Gap Size Penalty—0.05, Window Size=500 or the length of the subject amino acid sequence, whichever is shorter. If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. Only residue positions outside the N- and C-terminal ends of the subject sequence, as displayed in the FASTDB alignment, which are not matched/aligned with the query sequence are manually corrected for. No other manual corrections are to be made for the purposes of the present invention.

Naturally occurring protein variants are called "allelic variants," and refer to one of several alternate forms of a gene occupying a given locus on a chromosome of an organism. (Genes 11, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of polypeptides. For instance, one or more amino acids can be deleted from the N-terminus or C-terminus of a secreted protein without substantial loss of biological function. The authors of Ron et al., J. Biol. Chem. 268: 2984-2988 (1993), reported variant KGF proteins having hepanin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)). Moreover, ample evidence demonstrates that variants often retain a biological activity similar to that of the naturally occurring protein. For example, Gayle and co-workers (J. Biol. Chem. 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[most of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type. Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

"Fusion proteins", also known as chimeric proteins, are proteins created through the joining of two or more genes which originally coded for separate proteins. Translation of this fusion gene results in a single polypeptide with functional properties derived from each of the original proteins. Recombinant fusion proteins are created artificially by recombinant DNA technology for use in biological research or therapeutics. The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. A recombinant fusion protein is a protein created through genetic engineering of a fusion gene. This typically involves removing the stop codon from a cDNA sequence coding for the first protein (first partner), then appending the cDNA sequence of the second protein (second partner) in frame through ligation or overlap extension PCR. That DNA sequence will then be expressed by a cell as a single protein. The protein can be engineered to include the full sequence of both original proteins, or only a portion of either. If the two entities are proteins, linker (or "spacer") peptides can be added.

"Label" refers to agents that are capable of providing a detectable signal, either directly or through interaction with one or more additional members of a signal producing system. Labels that are directly detectable and may find use in the invention include fluorescent labels. Specific fluorophores include fluorescein, rhodamine, BODIPY, cyanine dyes and the like.

A "fluorescent label" refers to any label with the ability to emit light of a certain wavelength when activated by light of another wavelength.

"Fluorescence" refers to any detectable characteristic of a fluorescent signal, including intensity, spectrum, wavelength, intracellular distribution, etc.

"Detecting" fluorescence refers to assessing the fluorescence of a cell using qualitative or quantitative methods. In some of the embodiments of the present invention, fluorescence will be detected in a qualitative manner. In other words, either the fluorescent marker is present, indicating that the recombinant fusion protein is expressed, or not. For other instances, the fluorescence can be determined using quantitative means, e.g., measuring the fluorescence intensity, spectrum, or intracellular distribution, allowing the statistical comparison of values obtained under different conditions. The level can also be determined using qualitative methods, such as the visual analysis and comparison by a human of multiple samples, e.g., samples detected using a fluorescent microscope or other optical detector (e.g., image analysis system, etc.) An "alteration" or "modulation" in fluorescence refers to any detectable difference in the intensity, intracellular distribution, spectrum, wavelength, or other aspect of fluorescence under a particular condition as compared to another condition. For example, an "alteration" or "modulation" is detected quantitatively, and the difference is a statistically significant difference. Any "alterations" or "modulations" in fluorescence can be detected using standard instrumentation, such as a fluorescent microscope, CCD, or any other fluorescent detector, and can be detected using an automated system, such as the integrated systems, or can reflect a subjective detection of an alteration by a human observer.

The "green fluorescent protein" (GFP) is a protein, composed of 238 amino acids (26.9 kDa), originally isolated from the jellyfish *Aequorea victoria/Aequorea aequorea/Aequorea forskalea* that fluoresces green when exposed to blue light. The GFP from *A. victoria* has a major excitation peak at a wavelength of 395 nm and a minor one at 475 nm. Its emission peak is at 509 nm which is in the lower green portion of the visible spectrum. The GFP from the sea pansy (*Renilla reniformis*) has a single major excitation peak at 498 nm. Due to the potential for widespread usage and the evolving needs of researchers, many different mutants of GFP have been engineered. The first major improvement was a single point mutation (S65T) reported in 1995 in Nature by Roger Tsien. This mutation dramatically improved the spectral characteristics of GFP, resulting in increased fluorescence, photostability and a shift of the major excitation peak to 488 nm with the peak emission kept at 509 nm. The addition of the 37° C. folding efficiency (F64L) point mutant to this scaffold yielded enhanced GFP (EGFP). EGFP has an extinction coefficient (denoted ε), also known as its optical cross section of $9.13 \times 10^{-21}$ m$^2$/molecule, also quoted as 55,000 L/(mol·cm). Superfolder GFP, a series of mutations that allow GFP to rapidly fold and mature even when fused to poorly folding peptides, was reported in 2006.

The "yellow fluorescent protein" (YFP) is a genetic mutant of green fluorescent protein, derived from *Aequorea victoria*. Its excitation peak is 514 nm and its emission peak is 527 nm.

The Prm1 gene, also known as P1, encodes for protamine 1, also known as cysteine-rich protamine, sperm protamine P1 or testis specific protamine 1. Protamines are small, arginine-rich, nuclear proteins that replace histones late in the haploid phase of spermatogenesis. Mice, humans, and certain fish have 2 or more different protamines, whereas the sperm of bull, boar, rat, rabbit, guinea pig, and ram have one form of protamine. The 2 human protamines are denoted PRM1 and PRM2. Examples of protamines from fish are: salmine from salmon, clupeine from herring sperm (*Clupea*), iridine from rainbow trout, thinnine from tunafish (*Thunnus*), stelline from starry sturgeon (*Acipenser stellatus*) and scylliorhinine from dogfish (*Scylliorhinus*). The present invention encompasses fusion products of any protamine. Moreover, the present invention also encompasses fusion products of other gene products implicated in nuclear condensation during spermatogenesis or spermiogenesis, for instance transition proteins, and/or important for the proper development and functioning of spermatozoids.

Transition proteins (TPs) or transition nuclear proteins (TNPs) are proteins that are involved in the packaging of sperm nuclear DNA during spermiogenesis. They take the place of histones associated with the sperm DNA, and are subsequently themselves replaced by protamines. Examples of TNPs are TNP1 and TNP2

Spermatogenesis is the process by all males spermatogonia develop into mature spermatozoa. Spermatozoa are the mature male gametes in many sexually reproducing organisms. Thus, spermatogenesis is the male version of gametogenesis. In mammals it occurs in the male testes and epididymis. Spermatogenesis, which is essential for sexual reproduction, is highly dependent upon optimal conditions for the process to occur correctly, occurs in a stepwise fashion. Spermatocytogenesis is the male form of gametocytogenesis and results in the formation of spermatocytes possessing half the normal complement of genetic material. In spermatocytogenesis, a diploid spermatogonium which resides in the basal compartment of seminiferous tubules, divides mitotically to produce two diploid intermediate cell called a primary spermatocyte. Each primary spermatocyte then moves into the adluminal compartment of the seminiferous tubules and duplicates its DNA and subsequently undergoes meiosis I to produce two haploid secondary spermatocytes. This division implicates sources of genetic variation, such as random inclusion of either parental chromosomes, and chromosomal crossover, to increase the genetic variability of the gamete. Each cell division from a spermatogonium to a spermatid is incomplete; the cells remain connected to one another by bridges of cytoplasm to allow synchronous development. It should also be noted that not all spermatogonia divide to produce spermatocytes, otherwise the supply would run out. Instead, certain types of spermatogonia divide to produce copies of themselves, thereby ensuring a constant supply of gametogonia to fuel spermatogenesis.

Spermatidogenesis is the creation of spermatids from secondary spermatocytes. Secondary spermatocytes produced earlier rapidly enter meiosis II and divide to produce haploid spermatids. The brevity of this stage means that secondary spermatocytes are rarely seen in histological preparations.

During spermiogenesis, the spermatids begin to grow a tail, and develop a thickened mid-piece, where the mitochondria gather and form an axoneme. Spermatid DNA also undergoes packaging, becoming highly condensed. The DNA is packaged firstly with specific nuclear basic proteins, which are subsequently replaced with protamines during spermatid elongation. The resultant tightly packed chromatin is transcriptionally inactive. The Golgi apparatus surrounds the now condensed nucleus, becoming the acrosome. One of the centrioles of the cell elongates to become the tail of the sperm. Maturation then takes place under the influence of testosterone, which removes the remaining unnecessary cytoplasm and organelles. The excess cytoplasm, known as residual bodies, is phagocytosed by surrounding Sertoli cells in the testes. The resulting spermatozoa are now mature but lack motility, rendering them sterile. The mature spermatozoa are released from the protective Sertoli cells into the lumen of the seminiferous tubule in a process called spermiation. The non-motile spermatozoa are transported to the epididymis in testicular fluid secreted by the Sertoli cells with the aid of peristaltic contraction. While in the epididymis the spermatozoa gain motility and become capable of fertilisation. However, transport of the mature spermatozoa through the remainder of the male reproductive system is achieved via muscle contraction rather than the spermatozoon's recently acquired motility.

Homologs refer to proteins that share a common ancestor. Analogs do not share a common ancestor, but have some functional (rather than structural) similarity that causes them to be included in a class (e.g. trypsin like serine proteinases and subtilisin's are clearly not related—their structures out side the active site are completely different, but they have virtually geometrically identical active sites and thus are considered an example of convergent evolution to analogs).

There are two subclasses of homologs—orthologs and paralogs. Orthologs are the same gene (e.g. cytochome 'c'), in different species. Two genes in the same organism cannot be orthologs. Paralogs are the results of gene duplication (e.g. hemoglobin beta and delta). If two genes/proteins are homologous and in the same organism, they are paralogs.

The Rpgr gene, also known as COD1, CORDX1, CRD, OTTHUMP00000023140, PCDX, RP15, RP3, LRP3 or orf15, encodes for the retinitis pigmentosa GTPase regulator, also known as retinitis pigmentosa, cone dystrophy 1 (X-linked) or retinitis pigmentosa 3 GTPase regulator. This gene encodes a protein with a series of six RCC1-like domains (RLDs), characteristic of the highly conserved guanine nucleotide exchange factors. Mutations in this gene have been associated with X-linked retinitis pigmentosa (XLRP). Multiple alternatively spliced transcript variants that encode different isoforms of this gene have been reported.

In some embodiment of the invention, the genetically-modified non-human animal is a conditional transgene, for instance a "floxed" conditional knockout mouse established using the loxP/Cre recombinase system. The loxP/Cre recombinase system is well-known in the art (Kwan, Genesis, 32, 49-62 (2002) or (Rajewsky, et al., J Clin Invest, 98, 600-603 (1996)).

Unless otherwise defined, all technical and scientific terms used herein have the same meaning as commonly understood by one of ordinary skill in the art to which this invention belongs.

Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

EXAMPLES

Mouse Strains

C57BL6×DBA2 (BDF1) hybrid mice were obtained from the inventor's own breeding colony. CD-1 mice were obtained from Charles River Laboratories, Germany. All animal were housed in accordance with Swiss Federal Animal Protection Law. All experiments were carried out in accordance with Swiss Federal Guidelines under the auspices of the animal experiment licence granted by the Cantonal veterinary authority (Zurich licence 42/2005).

DNA

The mouse Protamine-1 (Prm1) locus including the promoter as well as the full length coding sequence was amplified by PCR from C57BL/6J genomic DNA using following primers: (5'Prm1—GTCTAGTAATGTCCAACACCTCCC; SEQ ID NO:1), 3'Prm1—AGATCTGTACAGGTGGCT-TGG; SEQ ID NO:2). The fragment was cloned in vector pGEM-T-easy (Invitrogen). The complete EGFP orf was inserted just upstream of the Prm1 STOP codon using inverted PCR and the following primers (Prm1CDS-rev—GTATTTTTTACACCTTATGGTGTATG; SEQ ID NO:3), Prm1UTR-fwd—TAGATGCACAGAATAGCAAGTCC (SEQ ID NO:4) to yield plasmid pGEM-Prm1-EGFP.

Generation of Transgenic Mice pGEM-Prm1-EGFP was liberalised using AseI and PvuII. The resulting 2.7 kb fragment was purified and microinjected into oocytes of BDF1 mice. Transgenic founder were identified be performing PCR on genomic DNA isolated form tail biopsies using following primers (GFP290-5'—GCAC-GACTTCTTCAAGTCCGCCATGCC; SEQ ID NO:5, GFP290-3'—GCGGATCTTGAAGTTCACCTTGATGCC; SEQ ID NO:6).

Vasectomies

Non-transgenic littermates were vasectomised and used as a control group in mating experiments involving genetically-vasectomised transgenic males. Vasectomy was carried out on males between the age of 6-8 weeks. The vasectomised males were allowed to recover for a period of 2 weeks prior to subsequent mating.

Mating/Plug Assays

Test male mice of 10-15 weeks were housed with two wild type (wt) CD1 females (Charles River Laboratories) for a test period of 5 days followed by a 2 day rest period during which the male and the females were separated into their own cages. Each test group consisted of three males aged 10-15 weeks at the beginning of the experiment. During the test period, females were checked every morning for the appearance of vaginal plug. Plugged females were removed and replaced by fresh females. The plugged females were maintained and housed individually in order to score for pregnancy. The complete experiment for every male consisted of 8 test rounds carried out over a 8 week period.

RNA Extraction

Following dissection, the testes were halved and preserved in 2 ml of RNA later (Ambion-Applied Biosystems). For each sample, half a testis was transferred in 600 μl RLT buffer 1% β-Mercaptoethanol (Qiagen) and homogenized using a Miller Mill MM 300 (Retsch). 2 homogenization rounds of 2 minutes at 20 Hz were performed. The total RNA from the homogenized testes was then extracted using the RNeasy Mini Kit (Qiagen) following the manufacturer's instructions. The total RNA of each testis was eluted in 50 μl RNAse-free water (Qiagen). The quality of each sample was assessed using a Bioanalyzer Nano Chip (Agilent), and the RNA concentration measured by spectrophotometry on a NanoDrop ND 1000 (Thermo Scientific).

Reverse Transcription

For each line, the total RNA was reversed transcribed into cDNA. 2 μl Oligo d(T)$^{12-18}$ Primer (Invitrogen), 2 μl 10 mM dNTP Mix (Invitrogen), were added to 500 ng total RNA and RNAse-free water (Qiagen) was added to each sample to obtain a final volume of 260. After a 5 min denaturation step at 65° C., 8 μl 5× First Strand Buffer (Invitrogen), 2 μl 0.1 μm DTT (Invitrogen), 2 μl RNAsin RNAse Inhibitor 40 U/μl (Promega), and 2 μl Superscript III Reverse Transcriptase 200 U/μl (Invitrogen), were added to each sample. For the negative controls 2 μl RNAse-free water were added instead of Superscript. The reverse transcription was carried out for 2 h at 50° C. and 15° min at 70° C.

Real-Time PCR

The expression levels of the Prm1 gene and the Prm1-EGFP fusion gene were assessed by Real-Time PCR. Two different Real-Time PCR experiments were performed using different sets of primers. For the Prm1 Real-Time PCR, the forward and the backwards primers were lying on the Prm1 gene (Prm1_FWD: 5'CCAGCACCATGGCCAGATAC3'; SEQ ID NO:7, and Prm1_BKD: 5'GATGTGGCGAGAT-GCTCTTG3'; SEQ ID NO:8). For the Prm1-EGFP Real-Time PCR the forward primer was lying on the Prm1 gene (Prm1_FWD: 5'CCAGCACCATGGCCAGATAC3'; SEQ ID NO:9), and the backward primer was lying on the EGFP gene (EGFP_BKD: 5'GGGTGTCGCCCTCGAACTTCAC-CTCGGCG3'; SEQ ID NO:10). In both experiments Real-time PCR reactions of the β-Actin gene were performed for normalization purposes. The primers for the β-Actin were: Actin-FWD (5'CATCCAGGCTGTGCTGTCCCTG-TATGC3'; SEQ ID NO:11) and Actin-BKD (5'GATCT-TCATGGTGCTAGGAGCCAGAGC3'; SEQ ID NO:12). For both Real-Time PCR reactions, the samples were prepared as follows: 2 μl cDNA, 10 μl Quantitect SYBR Green PCR MasterMix, 1 μl Forward primer 10 μM, 1 μl Backwards primer 10 μM, and 6 μl Rnase-Free water (Qiagen). The Real-Time PCR reactions were performed on a RotorGene Real-Time PCR machine (Corbett Research). The amplification program of the Prm1 fragment consisted in a 10 min denaturation phase at 94° C. followed by 40 cycles of 95° C. for 15 sec, 60° C. for 30 sec and 72° C. for 30 sec. The amplification program of the Prm1-EGFP fusion gene fragment consisted in a 10 min denaturation phase at 94° C. followed by 40 cycles of 95° C. for 15 sec, 60° C. for 30 sec and 72° C. for 45 sec.

Western Blotting

Testes were homogenized with RIPA buffer (50 mM Tris-Cl pH 7.4, 1% NP-40, 0.25% sodium deoxycholate, 150 mM NaCl). Protein concentration was determined with the BCA-Method (Pierce). Samples (10 µg of protein per lane) were subjected to SDS-PAGE and blotted onto PVDF membrane (Millipore) at 100 V for 1.5 h at 4° C. Immunodetection was performed with rabbit antibodies against GFP (Abcam: ab290) used at a 1/5000 dilution, followed by incubation with horse reddish peroxidase conjugated anti rabbit antibodies (Santa Cruz Biotechnology; sc-2030) at a 1/5000 dilution. Chemiluminescent visualization was performed as recommended by the supplier of the chemiluminescence blotting kit (Roche Diagnostics).

Histology and Microscopic Analysis

Testes and epididymi of mature transgenic males and their control siblings were dissected and fixed in 3% Paraformaldehyde in PBS for 24 hrs at 4° C. After washing with PBS, tissues were incubated in 30% sucrose (w/v in water) for 24 hours at 4° C. Subsequently, tissues were embedded in OCT embedding matrix and frozen on dry ice. Ten micrometer cryosections were generated using the Microm HM560 and subsequently embedded into Vectashield (Vector) mounting medium containing 4',6-diamidino-2-phenylindole (DAPI). Confocal microscopy was performed using the LSM510 META system (Zeiss).

ICSI

ICSI was carried out essentially as described (Kimura Y, Yanagimachi R., Biol Reprod. 1995 April; 52(4):709-20). Metaphase II (MII) Oocytes were collected from superovulated 8- to 12-week-old B6D2F1 females induced by intraperitoneal injection of 5 IU equine chorionic gonadotrophin (eCG), followed by injection of 5 IU human chorionic gonadotrophin (hCG) 48 hours later. Matured oocytes were collected from the ampullary region of oviducts 13-15 h after hCG injection. Oocytes were freed from cumulus cells by treatment with 0.1% bovine testicular hyaluronidase (359 units/mg solid) in HEPES-CZB medium, rinsed and kept at room temperature (26° C.) in fresh HEPES-CZB medium before sperm injection. Epididymal spermatozoa were collected from 8- to 12-week-old males by "swim-up" procedure in HEPES-CZB medium. In cases where no motile spermatozoa were observed, spermatozoa were released by dissociating the dense sperm mass in HEPES-CZB medium. Spermatozoa were collected and placed in a 20 µl droplet containing a 12% (w/v) polyvinylpyrrolidone (PVP; Mr 360,000) prepared in HEPES-CZB. A single spermatozoon was drawn, tail first, into the injection pipette in such a way that its neck was at the opening of the pipette. The head was separated from the tail by applying a few piezo-pulses to the neck region. The tail-less spermatozoon was injected into an oocyte.

Embryo Culture:

All oocytes used for ICSI experiments were cultured for 5 days in M16 medium (Sigma) at 37° C. under 5% $CO_2$ in air. Oocyte activation as judged by appearance well-developed pronuclei and a distinct second polar body as well as subsequent embryonic development was followed with daily observations.

Results

Overexpression of Prm1-EGFP Causes Dominant Male Sterility

Figure 1:
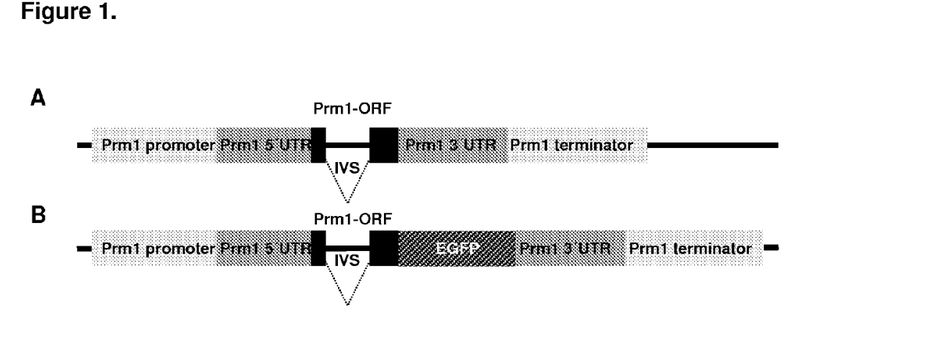
FIG. 1: Schematic diagram of the endogenous mouse Prm1 locus (A) and of the Prm1-EGFP transgene (B). Promoter and transcribed elements: untranslated regions (UTR), protein coding region (ORF) and introns (IVS) are indicated.
Figure 2:
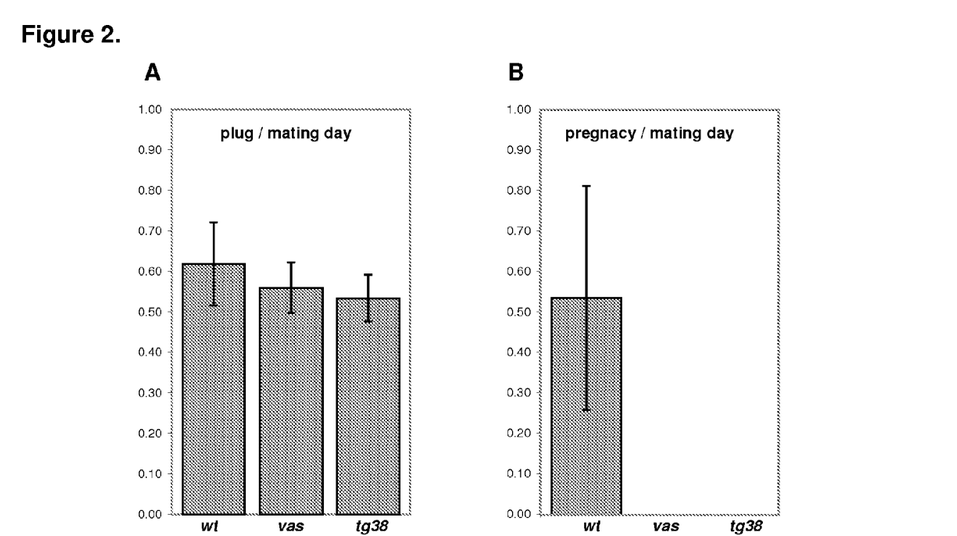
Figure 3:
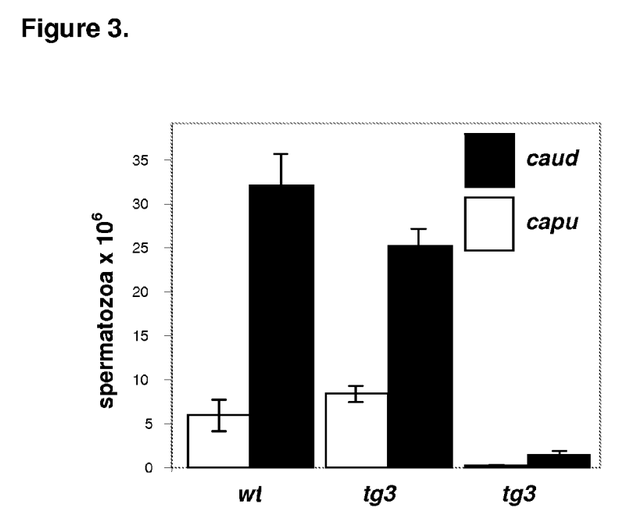
FIG. 3: Sperm counts in caput and caudal epididymi of wild-type (wt) and transgenic (tg38) male mice (average and standard deviation; n=3 per genotype).
Figure 4:
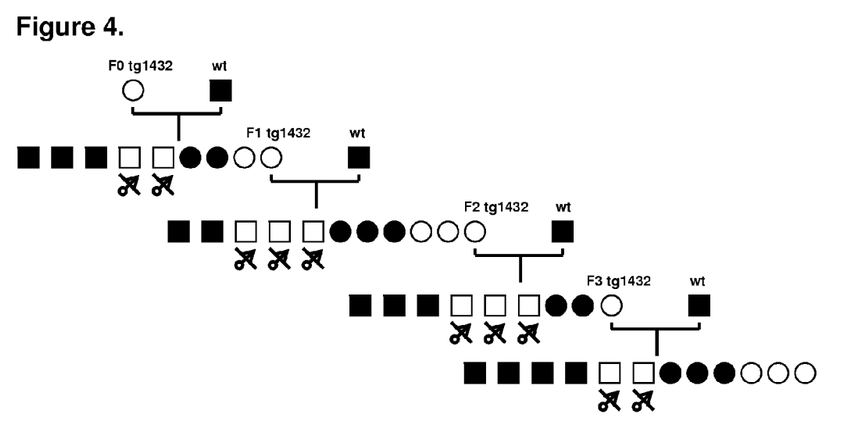
FIG. 4: Transgenic line tg1432—linking dominant male sterility to full-body EGFP expression. Part of the pedigree tree for line tg1432. Males and females are indicated by squares and circles, respectively. Green fluorescence caused by expression of the CAG-EGFP transgene is by white symbols. In all cases dominant male sterility was linked to full-body EGFP expression indicating tight genetic linkage of CAG-EGFP and Prm1-EGFP transgenes.

The inventor's approach aimed at impairing the maturation and production of spermatozoa by interfering with the histone-to-protamine exchange during the final stages of spermatogenesis. Towards this goal, the present inventors set out to create a dominant-negative variant of the Prm1 protein that would interfere with either proper DNA condensation during sperm maturation and/or decondensation following fertilisation. They used the Prm1 genomic locus as a template to generate a transgenic construct containing the regulatory elements of the mouse Prm1 gene (promoter and 3'UTR) to selectively overexpress a fusion protein of Prm1 and EGFP in elongating spermatids (FIG. 1). The present inventors inserted the EGFP coding sequence following the last amino acid coding triplet of the Prm1 protein. The resulting construct was linearised and injected into pronuclei of BDF1 oocytes resulting in a total of seven transgenic F0 founders, three females and four males respectively. All the attempts to breed the four male founders failed despite repeated successful matings as demonstrated by appearance of copulatory plugs. The three female founders bred successfully with BDF1 male mice giving rise to three transgenic lines, Prm1-EGFP tg36 (tg36), Prm1-EGFP tg37 (tg37), and Prm1-EGFP tg38 (tg38). Regular breedings showed that hemizygous males from the tg38 consistently failed to produce offspring. The sterility of the line tg38 was tested in more detail. The present inventors assessed the mating performance of hemizygous tg38 males as well as of normal and vasectomised males that served as positive and negative controls respectively. These analyses showed that though males from all genotypes could efficiently produce copulatory plugs, only normal non-transgenic littermates could impregnate their partners and produce normal size litters.

Dominant Sterility Correlates with Prm1-EGFP Expression Levels

Different transgenic lines generated by pronuclear microinjection frequently show different levels of transgene expression. Differences between founder lines can result from differences in the transgene copy number or due to position effect variegation. The present inventors investigated mRNA and protein levels of the Prm1-EGFP transgene. Quantitative real time PCR performed on total RNA isolated from testes of 3 month-old male mice showed no difference in total levels of Prm1 message between transgenic lines and wild-type mice indicating that any differences in Prm1 EGFP transcript level were masked by much higher levels of the endogenous Prm1 message. However, comparison of Prm1-EGFP RNA levels between the transgenic lines showed that Prm1-EGFP transcripts levels were roughly 7-fold higher in tg38 males compared with others. This difference correlated with approximately 30 fold higher levels of the fusion protein in whole testis extracts as detected in western blot analyses using an anti-EGFP antibody. The higher levels of Prm1-EGFP expression correlate with and are most likely the cause of the dominant sterility phenotype observed in line tg38.

Overexpression of Prm1-EGFP Induces Spermiation Defects During Spermiogenesis

To determine the possible mechanism underlying the sterility of line tg38, the present inventors performed morphological and histological analysis of testes and epididymi. The overall architecture and the tubular structures of both organs was normal in transgenic lines. In general, EGFP levels were high in testes of tg38, consistent with the Prm1-EGFP protein levels measured in testis extracts. In caudal epididymi EGFP levels were greatly reduced in tg38. Histological analyses revealed that the overall low EGFP levels in caudal epididymi of tg38 males correlated with a strongly reduced number of spermatozoa. Sperm quantification analyses of epididymal tissues confirmed that the number of spermatozoa was strongly reduced in both caudal and caput epididymi of tg38 males. These data suggest that a high level of Prm1-EGFP expression does not necessarily impair the development of spermatids but affects sperm viability.

Timely translation of the Prm1 message is crucial for proper spermatid development (Lee K, Haugen H S, Clegg C H, Braun R E. Proc Natl Acad Sci USA. 1995 Dec. 19; 92(26):12451-5). In transgenic approaches, translation of Prm1 at the time of its transcription affects the morphogenesis of spermatid heads in early elongating spermatids and causes a failure to release spermatids from the seminiferous epithelium. In more highly expressing transgenic animals, premature translation of Prm1 caused a complete spermatogenic arrest at the round spermatid stage (Lee et al.). In light of these findings, the present inventors analysed the timing of Prm1-EGFP expression in the tg38 line. EGFP signal is weakly detectable in elongating spermatids at stage XII of the seminiferous epithelium. EGFP expression increases from stage I onwards, mimicking expression of endogenous Prm1 protein. These data indicate that the long Prm1-EGFP transcript is properly subjected to translational repression via its 3'UTR, in the tg38 line. Quantitative imaging analyses revealed high levels of Prm1-EGFP in tg38 elongated spermatids (e.g. at stage VI and IX). Moreover, the release of elongated spermatids into the lumen of the seminiferous tubules was partially impaired in tg38 males as indicated by the presence of highly condensed EGFP-positive nuclei at all stages of the seminiferous epithelium. In summary, Prm1-EGFP overexpression does not fully block spermiogenesis as observed in transgenic animals prematurely expressing Prm1. Instead, it affects the development of elongated spermatids in a more subtle manner.

Overexpression of Prm1-EGFP Impairs Developmental Potential of Spermatozoa

To test the developmental potency of tg38 spermatozoa, the present inventors performed in vitro fertilisation (IVF). Unlike spermatozoa of wild-type mice, those of tg38 males failed to fertilize oocytes since they were completely immotile. In order to ascertain whether the tg38 spermatozoa are in principle capable of fertilising an oocyte and supporting early embryonic development, the present inventors performed Intracytoplasmic Sperm Injection (ICSI) experiments using sperm of wild-type and both transgenic lines (Table 1). The tg38 spermatozoa failed in the majority of attempts to activate the oocyte and to support embryonic development.

Linking Dominant Sterility to Full-Body EGFP as a Phenotypic Marker.

The nature of the Prm1-EGFP based male sterility requires that the transgene is transmitted in crosses between hemizygous transgenic females and wild-type males. Such breeding scheme requires conventional genotyping since only 50% of the progeny carries the Prm1-EGFP transgene. In order to simplify the breeding and to eliminate the need for taking biopsies, the present inventors generated transgenic lines where the Prm1-EGFP transgene is genetically linked to the CAG-EGFP transgene that is strongly expressed in all mouse tissues (Okabe M, Ikawa M, Kominami K, Nakanishi T, Nishimune Y. FEBS Lett. 1997 May 5; 407(3):313-9.) and thus can serve as an easy phenotypic marker. Genetic linking was achieved by co-injection of linearised plasmid DNA of the Prm1-EGFP and CAG-EGFP transgenes. The present inventors obtained several transgenic founders containing both transgenes. One of the female double-transgenic founders gave rise to the Prm1-EGFP tg1432 (tg1432) mouse line in which the dominant male sterility reliably co-segregated with full-body EGFP expression. Currently, line tg1432 has been backcrossed for 4 generations yielding over 200 male offspring. In all cases, full-body EGFP expression co-segregated with Prm1-EGFP mediated male sterility.

The above results thus show that proper remodelling of chromatin states during spermiogenesis is essential for male fertility. Previous studies indicated that particularly the timing of expression and proper gene dosage of Protamine 1 and 2 are essential (Cho C, Willis W D, Goulding E H, Jung-Ha H, Choi Y C, Hecht N B, Eddy E M. Nat. Genet. 2001 May; 28(1):82-6; Lee K, Haugen H S, Clegg C H, Braun R E. Proc Natl Acad Sci USA. 1995 Dec. 19; 92(26):12451-5). Here the present inventors show that increased expression of a Prm1-EGFP fusion protein at the time of remodelling surprisingly induces dominant male sterility. Prm1-EGFP-mediated expression does not result in premature translation of the message indicating that the long transgene is subjected to proper translational control mediated by the Prm1 3'UTR. Prm1-EGFP overexpression is associated with defects in spermiation, impaired motility and increased lethality of spermatozoa in the epididymis. Furthermore, Prm1-EGFP positive spermatozoa do not support early pre-implantation development showing that high levels of the fusion protein impairs the remodelling of the paternal genome during spermiogenesis and/or during the decondensation of the sperm head and formation of the male pronucleus in the one-cell embryo. Extensive experiments are required to elucidate the changes in chromatin states and nuclear organization in Prm1-EGFP bearing spermatozoa that underlie their inability to support early embryogenesis. Nonetheless, regardless of its mode of action, the dominant male-sterility caused by the overexpression of Prm1-EGFP can serve as a reliable and simple replacement of the surgical vasectomy procedure.

TABLE 1

Developmental capacities of spermatozoa following ICSI

| Sperm Strain | oocytes injected (=n) | oocytes surviving (% injected) | Embryo Development | | | |
|---|---|---|---|---|---|---|
| | | | 2 Pronuclei 6 h (% surviving) | 2-cell 22 h (% surviving) | Morula 76 h (% surviving) | Blastocyst 120 h (% surviving) |
| Wt-BDF1 | 68 (2) | 54 (79.4) | 54 (100) | 52 (96.3) | 42 (77.8) | 33 (61.1) |
| 38 | 67 (2) | 62 (92.5) | 11 (17.7) | 9 (14.5) | 4 (6.5) | 2 (3.2) |

BDF1 oocytes were isolated at the metaphase II stage and injected with sperm heads of the indicated strain. The embryos were cultured for 5 days and their development was scored daily at times indicated.

Mutations resulting in male sterility have been previously described and most of them can be assigned to genes controlling DNA recombination, DNA repair or differentiation of the male reproductive tract or the male germline (Bellve A R., The Molecular Biology of Mammalian Spermatogenesis, ed. Finn C A., Oxford Univ. Press, London, Vol. 1, pp. 159-261; Brugmans L, Kanaar R, Essers J. Mutat Res. 2007 Jan. 3; 614(1-2):95-108; Jaroudi S, SenGupta S. Mutat Res. 2007 January-February; 635(1):53-77). Unfortunately, these mutations are associated with decreased viability, susceptibility to cancer or other diseases. In addition, strains harbouring such mutations are not good candidates for vasectomy replacement since these recessive traits require breeding and reliable genotyping of heterozygous (fertile) versus homozygous (sterile) male mutant mice. Although dominant mutations causing male sterility have also been described, also none of them appear to be ideally suited for the purpose of replacing surgically vasectomised males in a laboratory environment. Such mutants include the Dominant spermiogenesis defect (Dspd) which results from a reciprocal translocation between chromosomes 14 and 7 (Kai M, Irie M, Okutsu T, Inoue K, Ogonuki N, Miki H, Yokoyama M, Migishima R, Muguruma K, Fujimura H, Kohda T, Ogura A, Kaneko-Ishino T, Ishino F. Biol Reprod. 2004 April; 70(4):1213-21. Epub 2003 Dec. 26) as well as two randomly generated insertional mutations named Lacking vigorous sperm (Lvs) (Magram J, Bishop J M. Proc Natl Acad Sci USA. 1991 Nov. 15; 88(22): 10327-31) and *Dominant male sterility* (Dms) (Meng X, Akutsu H, Schoene K, Reifsteck C, Fox E P, Olson S, Sariola H, Yanagimachi R, Baetscher M. Biol Reprod. 2002 March; 66(3):726-34), respectively. Since the genes causing the sterility have not been identified, it is impossible to reproduce the phenotype in other strains. Dominant male-sterility has also been described in mice overexpressing transgenes. For example, ubiquitous overexpression of the Retinoic acid receptor alpha (Rarα) causes dominant male-sterility due to severe malformation of the epithelium of the reproductive tract (Costa S L, Boekelheide K, Vanderhyden B C, Seth R, McBurney M W. Biol Reprod. 1997 April; 56(4):985-90). Unfortunately, the perturbation of the epithelium also prevents the formation of the ejaculate. Hence, sterile males fail to produce a copulatory plug upon mating making the identification of pseudopregnant females virtually impossible. Overexpression of the Retinits pigmentosa GTPase regulator (Rpgr) protein leads also to male infertility due to defects in flagellum assembly (Brunner S, Colman D, Travis A J, Luhmann U F, Shi W, Feil S, Imsand C, Nelson J, Grimm C, Rülicke T, Fundele R, Neidhardt J, Berger W. Biol Reprod. 2008 October; 79(4):608-17). Here the transgenic mice and their F1 offspring did show dominant male sterility. Instability of the transgenic locus in subsequent generations, however, raises doubts about using the Rpgr overexpressing mice as vasectomy replacements. In conclusion, none of these mutant or transgenic mouse models display dominant sterility with full penetrance in combination with a normal mating behaviour as exhibited by the Prm1-EGFP tg38 and tg1432 lines.

Additional advantage of using Prm1-EGFP transgene as vasectomy replacement is the genetic linkage of the trait to a phenotypical marker in the form of ubiquitous EGFP expression. This strategy removes the burden of identification of transgenic offspring by standard genotyping methods. To maintain the double transgenic Prm1-EGFP, CAG-EGFP tg1432 strain, hemizygous transgenic females need to be bred to non-transgenic males. Whereas 50% of the offspring will be transgenic, the remaining males and females will be wild-type. These wild-type mice can be used for other purposes such as foster mothers, sentinels or breeding studs. The versatility in applications of the double transgenic Prm1-EGFP; CAG-EGFP mice will thus guarantee its efficient usage in common transgenesis practise. Furthermore, the simplicity of using Prm1-EGFP transgenes as means for inducing dominant male sterility suggests that the method can be extended to other relevant livestock or pet species where uncontrolled breeding of males needs to be prevented as described hereinabove

The invention claimed is:

1. A genetically-modified non-human animal whose somatic and germ cells contain an exogenous gene encoding a recombinant fusion protein, wherein the recombinant fusion protein consists of a wild type gene operably-linked to a label so that the structure or function of said wild type gene is disrupted by the attachment of said label, wherein the gene encodes for a recombinant fusion protein encoding a Prm1 gene product, wherein the genetically-modified non-human animal is a mouse, and wherein the presence and expression of said recombinant fusion protein renders said genetically-modified non-human animal sterile.

2. The genetically-modified non-human animal of claim 1, wherein said gene encoding a recombinant fusion protein is dominant and wherein the presence, and expression, of only one allele of said recombinant fusion protein renders said genetically-modified non-human animal sterile.

3. The genetically-modified animal of claim 1, wherein the expression product of said gene encoding a recombinant fusion protein hinders spermatogenesis or modifies spermatozoa in such a way that they do not support embryonic development after fertilization.

4. The genetically-modified non-human animal of claim 1 wherein said animal is a sterile male and is for use to induce pseudopregnancy in surrogate mothers.

5. The genetically-modified non-human animal of claim 1, wherein the recombinant fusion protein is only expressed upon addition, or expression, of a further component.

6. The genetically-modified non-human animal of claim 5, wherein the further component is doxycycline or a CRE recombinase.

7. The genetically-modified non-human animal of claim 1, wherein one of the fusion partner is a fluorescent label.

8. The genetically-modified non-human animal of claim 1, wherein at least some of the somatic cells of said genetically-modified non-human animal express a label if the gene coding for the recombinant fusion protein is present, and wherein the presence of said label allows for a rapid selection of the genetically-modified non-human animal carrying the gene encoding for the recombinant fusion protein.

9. The genetically modified non-human animal of claim 8, wherein the label is a fluorescent label.

10. The animal of claim 7, wherein the fluorescent label is EGFP.

11. The animal of claim 9, wherein the fluorescent label is EGFP.

12. A method of generating a chimaeric animal comprising obtaining a pre-implantation embryo obtained from the animal of claim 1.

13. The genetically modified non-human animal of claim 1, wherein when the gene encoding a recombinant fusion protein is present, the animal may be selected by an outward physical phenotype, wherein the outward physical phenotype is curly hair or fur color.

* * * * *

UNITED STATES PATENT AND TRADEMARK OFFICE
CERTIFICATE OF CORRECTION

PATENT NO.       : 8,633,348 B2                                                                  Page 1 of 1
APPLICATION NO.  : 13/392145
DATED            : January 21, 2014
INVENTOR(S)      : Pelczar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 41 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 12

<210> SEQ ID NO 1
<211> LENGTH: 24
<212> TYPE: DNA
<213> ORGANISM: Mus musculus

<400> SEQUENCE: 1
gtctagtaat gtccaacacc tccc                                            24

<210> SEQ ID NO 2
<211> LENGTH: 21
<212> TYPE: DNA
<213> ORGANISM: Mus musculus

<400> SEQUENCE: 2
agatctgtac aggtggcttg g                                               21

<210> SEQ ID NO 3
<211> LENGTH: 26
<212> TYPE: DNA
<213> ORGANISM: Mus musculus
```

-continued

```
<400> SEQUENCE: 3 gtattttta caccttatgg tgtatg                                           26

<210> SEQ ID NO 4
<211> LENGTH: 23
<212> TYPE: DNA
<213> ORGANISM: Mus musculus

<400> SEQUENCE: 4
tagatgcaca gaatagcaag tcc                                             23

<210> SEQ ID NO 5
<211> LENGTH: 27
<212> TYPE: DNA
<213> ORGANISM: Mus musculus

<400> SEQUENCE: 5
gcacgacttc ttcaagtccg ccatgcc                                         27

<210> SEQ ID NO 6
<211> LENGTH: 27
<212> TYPE: DNA
<213> ORGANISM: Mus musculus

<400> SEQUENCE: 6
gcggatcttg aagttcacct tgatgcc                                         27

<210> SEQ ID NO 7
<211> LENGTH: 20
<212> TYPE: DNA
<213> ORGANISM: Mus musculus

<400> SEQUENCE: 7
ccagcaccat ggccagatac                                                 20

<210> SEQ ID NO 8
<211> LENGTH: 20
<212> TYPE: DNA
<213> ORGANISM: Mus musculus

<400> SEQUENCE: 8
gatgtggcga gatgctcttg                                                 20

<210> SEQ ID NO 9
<211> LENGTH: 20
<212> TYPE: DNA
<213> ORGANISM: Mus musculus

<400> SEQUENCE: 9
ccagcaccat ggccagatac                                                 20

<210> SEQ ID NO 10
<211> LENGTH: 29
<212> TYPE: DNA
<213> ORGANISM: Mus musculus

<400> SEQUENCE: 10
gggtgtcgcc ctcgaacttc acctcggcg                                       29

<210> SEQ ID NO 11
<211> LENGTH: 27
<212> TYPE: DNA
<213> ORGANISM: Mus musculus
```

```
<400> SEQUENCE: 11
catccaggct gtgctgtccc tgtatgc                                    27

<210> SEQ ID NO 12
<211> LENGTH: 27
<212> TYPE: DNA
<213> ORGANISM: Mus musculus

<400> SEQUENCE: 12
gatcttcatg gtgctaggag ccagagc                                    27
```